(12) United States Patent
Sambusseti

(10) Patent No.: US 10,898,615 B2
(45) Date of Patent: Jan. 26, 2021

(54) RESORBABLE DEVICE FOR THE RECONSTRUCTION OF CARTILAGE

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 0 days.

(21) Appl. No.: 15/124,069

(22) PCT Filed: Apr. 2, 2015

(86) PCT No.: PCT/IB2015/052436
§ 371 (c)(1),
(2) Date: Sep. 7, 2016

(87) PCT Pub. No.: WO2015/155651
PCT Pub. Date: Oct. 15, 2015

(65) Prior Publication Data
US 2017/0014551 A1    Jan. 19, 2017

(30) Foreign Application Priority Data

Apr. 8, 2014 (IT) .............................. MI2014A0647

(51) Int. Cl.
| | | |
|---|---|---|
| *A61L 27/58* | (2006.01) | |
| *A61L 27/18* | (2006.01) | |
| *A61L 31/06* | (2006.01) | |
| *A61L 31/10* | (2006.01) | |
| *A61L 27/34* | (2006.01) | |
| *A61L 31/14* | (2006.01) | |
| *A61L 27/22* | (2006.01) | |
| *A61L 27/24* | (2006.01) | |
| *A61L 27/36* | (2006.01) | |

(52) U.S. Cl.
CPC .............. *A61L 27/58* (2013.01); *A61L 27/18* (2013.01); *A61L 27/225* (2013.01); *A61L 27/24* (2013.01); *A61L 27/34* (2013.01); *A61L 27/3616* (2013.01); *A61L 31/06* (2013.01); *A61L 31/10* (2013.01); *A61L 31/148* (2013.01); *A61L 2430/06* (2013.01)

(58) Field of Classification Search
None
See application file for complete search history.

(56) References Cited

U.S. PATENT DOCUMENTS

| | | | | |
|---|---|---|---|---|
| 3,875,937 | A | * | 4/1975 | Schmitt ............. A61F 13/00063 128/DIG. 8 |
| 2004/0010320 | A1 | | 1/2004 | Huckle et al. |
| 2006/0252981 | A1 | | 11/2006 | Matsuda et al. |
| 2007/0041952 | A1 | * | 2/2007 | Guilak ................ A61F 2/30965 424/93.7 |
| 2007/0128155 | A1 | | 6/2007 | Seyedin et al. |
| 2009/0246238 | A1 | * | 10/2009 | Gorman .................. A61L 15/26 424/402 |
| 2011/0223253 | A1 | | 9/2011 | Gisselfaelt et al. |

FOREIGN PATENT DOCUMENTS

| | | |
|---|---|---|
| JP | 2001340446 A | 12/2001 |
| JP | 2003038635 A | 2/2003 |
| JP | 2003245338 A | 9/2003 |
| JP | 2006508773 A | 3/2006 |
| JP | 2009518132 A | 5/2009 |
| WO | 0185226 A1 | 11/2001 |
| WO | 20040050133 A2 | 6/2004 |
| WO | 2007067637 A2 | 6/2007 |
| WO | 20110064110 A1 | 6/2011 |

OTHER PUBLICATIONS

Wang et al.(Journal of the mechanical behavior of medical materials 4, 922-932, 2011) Applications of Knitted. . . .*
Hannouche et al. (Tissue Engineering, 13(1), 87-99, 2007).*
International Search Report and Written Opinion dated Jun. 30, 2015 for PCT/IB2015/052436 to Antonio Sambusseti filed Apr. 2, 2015.
Office Action dated May 8, 2018 from Japanese Patent Application No. 2016-561359 to Antonio Sambusseti.
Polyglycolic Acid, Science Direct, URL: <https://www.sciencedirect.com/topics/engineering/polyglycolic-acid >, retrieved from the Internet Jul. 6, 2020.
Warp Knitting, Wikipedia, URL: <https://en.wikipedia.org/wiki/Warp_knitting >, retrieved from the Internet Jul. 3, 2020.

\* cited by examiner

*Primary Examiner* — Tigabu Kassa
(74) *Attorney, Agent, or Firm* — Vorys, Sater, Seymour and Pease LLP

(57) ABSTRACT

A resorbable device for the reconstruction of cartilage includes a piece of fabric made of PGA, which can be impregnated with patient blood and fixable to a bone at an articulation, the piece preferably being impregnated with collagen.

18 Claims, 3 Drawing Sheets

RESORBABLE DEVICE FOR THE RECONSTRUCTION OF CARTILAGE

CROSS-REFERENCE TO RELATED APPLICATIONS

This is a § 371 National Stage Application of International Application No. PCT/IB2015/052436 filed on Apr. 2, 2015, claiming the priority of Italian Patent Application No. MI2014A000647 filed on Apr. 8, 2014.

FIELD OF THE INVENTION

The present invention refers to a resorbable device for the reconstruction of cartilage of an articulation.

By way of example, the present invention is applicable to the reconstruction of cartilage damaged by trauma or degenerative diseases of articulations such as the knee, shoulder or still others.

BACKGROUND OF THE INVENTION

According to that known, in the case of an articular trauma or degenerative articular pathologies that determine a lesion of the cartilage tissues, it is necessary to surgically operate in order to restore the situation and allow an easy movement of the articulation.

In detail, during the surgical operation, executed by means of arthrotomy or arthroscopy, cartilage fragments and damaged cartilage are removed from the articular zone.

After this cleaning and leveling operation, it is necessary to draw blood from the patient and place the blood in a culture in order to obtain protein-rich plasma therefrom.

Subsequently, a matrix is implanted on the bone of the affected articulation and it is irrigated with the culture.

The patient thus operated must be subjected to other infiltrations of autologous blood or additional cultures over time starting from the time of operation, in order to complete the reconstruction.

This technique has several significant disadvantages.

Indeed, first of all, cartilage cell culture is a very costly process and requires a long time for completion.

In addition, this technique obliges the patent to undergo a multi-phase therapy. Indeed, the grafting of the cultivated cells occurs after the surgical operation and further support therapies may also be required during the tissue regeneration phase.

Similar drawbacks can be found in WO01/85226 which describes a method for obtaining a tissue graft for the reconstruction of an injured connective tissue and, more in particular, it discloses the use of a scaffold which has to be implanted in direct contact or adjacent to a mature/immature target tissue for a period of time suitable for allowing the cells of said target tissue to infiltrate the scaffold and then removing the implant and implanting it in the patient in the site to be repaired.

Another known solution, showing the same drawbacks as above, is disclosed by US2011/223253 which refers to an osteochondral implant physically stabilized comprising a biodegradable porous resilient matrix, with said implant having a substantially cylindrical shape and suitable to be inserted in proper bores surgically formed in the bone to be treated and, moreover, with said implant which is stiffened by means of blood coagulated in vitro before the implantation.

SUMMARY OF THE INVENTION

In this context, the technical task underlying the present invention is to propose a resorbable device for the reconstruction of cartilage that overcomes the drawbacks of the abovementioned prior art.

In particular, object of the present invention is to provide a resorbable device for the reconstruction of cartilage that allows a quick reconstruction of the cartilage of an articulation of a patient and which allows a consistent decrease of the times and discomfort for the patient himself.

The specified technical task and object are substantially achieved by a resorbable device for the reconstruction of cartilage comprising the technical characteristics set forth in one or more of the enclosed claims.

BRIEF DESCRIPTION OF THE DRAWINGS

Further characteristics and advantages of the present invention will be clearer from the exemplifying and hence non-limiting description of a preferred but not exclusive embodiment of a resorbable device for the reconstruction of cartilage, as illustrated in the set of drawings in which.

DETAILED DESCRIPTION OF THE PREFERRED EMBODIMENTS

With reference to the enclosed drawings, reference number 1 overall indicates a resorbable device for the reconstruction of cartilage in accordance with the present invention.

Figure 1:
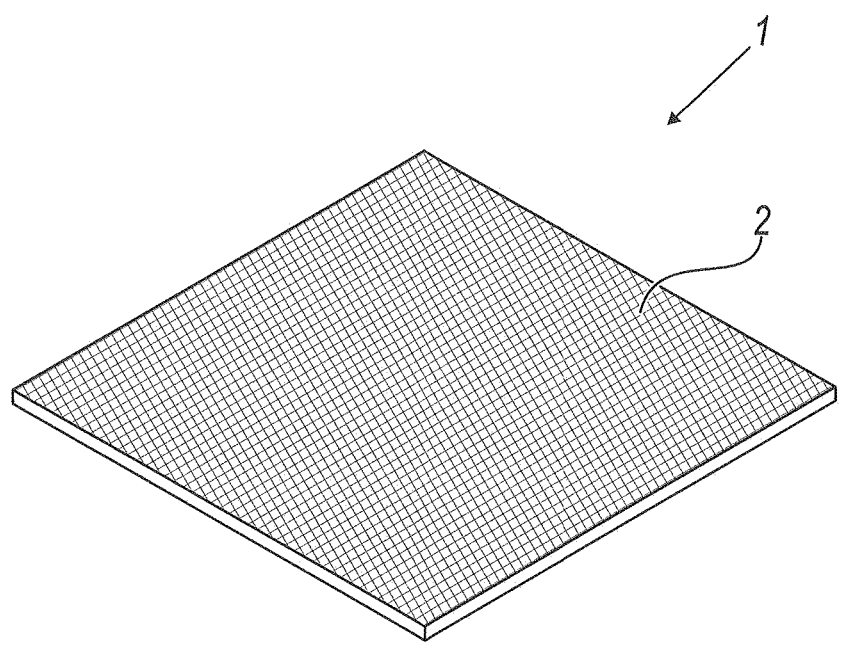
FIG. 1 is schematic perspective view of a resorbable device for the reconstruction of cartilage in accordance with the present invention.
Figure 2:
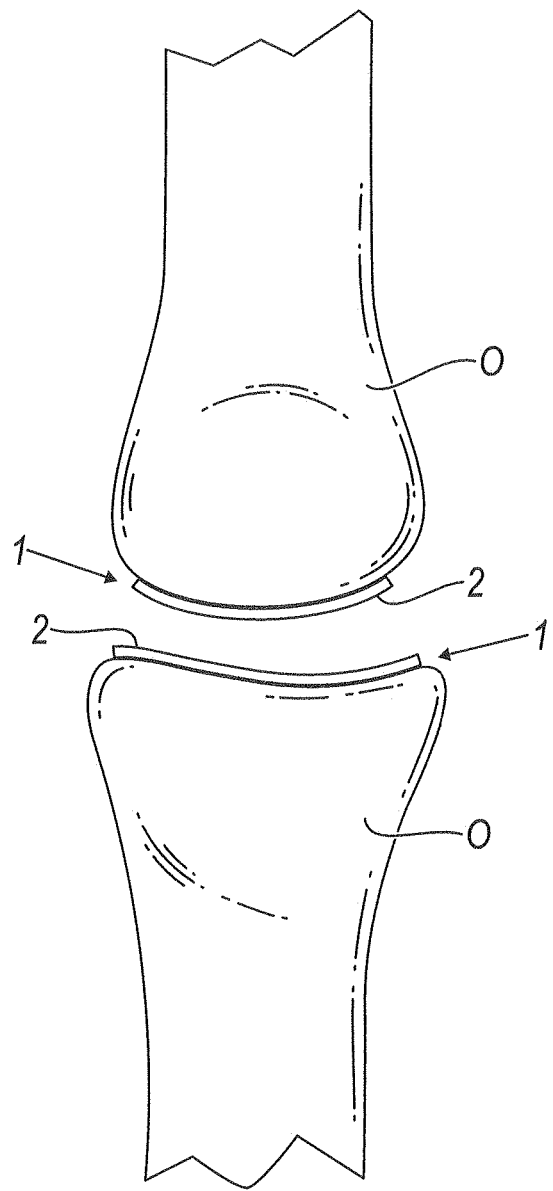
FIG. 2 is a schematic view of the device of FIG. 1 installed in an articulation of a patient.
Figure 3:
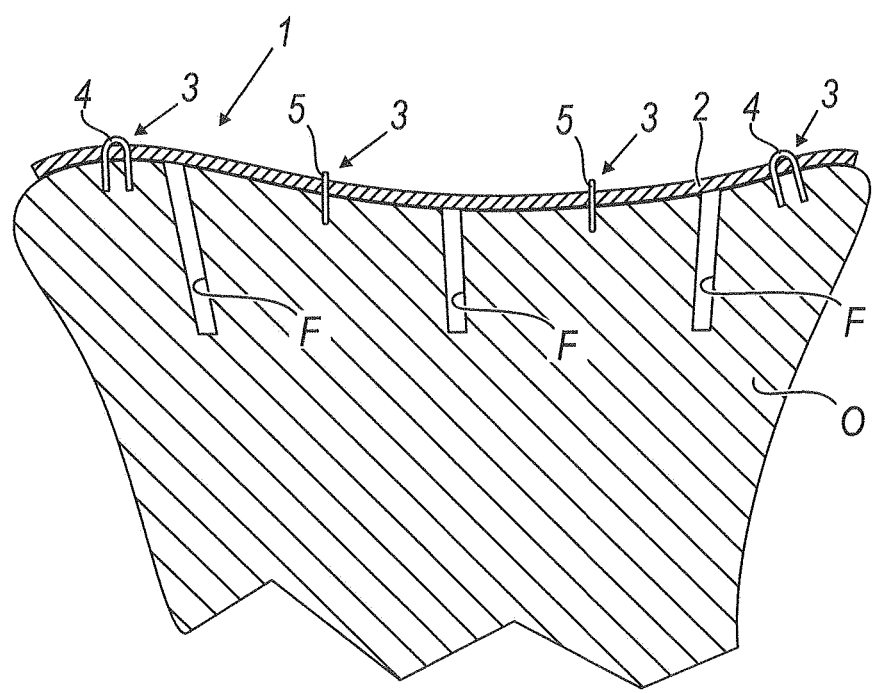
FIG. 3 is an enlarged view of FIG. 2.

The device 1 comprises a piece of fabric 2. For example, the device 1 is a single layer of the piece of fabric 2, as shown in FIGS. 1-3. As will be clearer hereinbelow, the piece 2 is intended to be fixed on a bone "O" of a patient articulation.

In particular, the fabric is made of PGA (polyglycolide or poylglycolic acid), preferably homopolymer. Still more in particular, the fabric is made with an ultralight monofilament or thread deriving from PGA fibers.

PGA is a highly biocompatible and resorbable polymer. In detail, the resorption time of PGA is approximately one month.

The fabric of the piece 2 can be obtained by weaving the PGA thread in various ways, giving rise to a knitted fabric, a woven fabric or a non-woven fabric.

Preferably, the fabric is a knitted fabric, still more preferably a warp knitted fabric.

In such case, the fabric has a rougher surface capable of assuming a net configuration with sufficiently small meshes.

In detail, its weft is such that its interstitial space is less than 200 µm, preferably around 160 µm, corresponding to an average area of the holes equal to approximately 0.02 mm$^2$. This ensures good protection of the tissues covered by the piece 2.

Furthermore, the fabric is preferably textured so as to give it even greater surface roughness and greater rigidity and impermeability.

In addition, the fabric is preferably obtained with a thread having a density comprised between 50 and 200 denier.

Merely by way of example, the fabric has a thickness substantially comprised between 0.3 mm and 0.6 mm, more preferably comprised between 0.4 mm and 0.53 mm, and still more preferably is substantially 0.45 mm.

According to the preferred embodiment, the piece 2 has square form. Preferably, the side of the piece 2 substantially measures 10 cm.

During use, the user can cut a portion of the piece according to a shape and size that are suitable for the zone to be treated.

Preferably, the piece 2 is impregnated with collagen. Still more preferably, the piece 2 is impregnated with purified porcine collagen.

The device 1 also comprises constraining means 3 necessary for fixing the piece 2 to the bone.

Preferably, the constraining means 3 comprise fibrin glue which is affixed in specific points between the piece 2 and the bone "O" in a manner so as to obtain the fixing.

In addition, the constraining means 3 also comprise screws and/or anchors and/or staples and/or pins. In FIG. 3, two staples 4 and one pin 5 are illustrated.

The screws and/or anchors and/or staples 4 and/or pins 5 are made of resorbable material. Preferably, the screws and/or anchors and/or staples 4 and/or pins 5 are made of PGA/PLA.

According to a method for applying device 1 according to the present invention, the piece 2 is first immersed in the blood of the patient himself.

The blood necessary for this phase can be drawn during the operation by means of syringe.

In case of bleeding of the operating field, the blood deriving from such bleeding can be advantageously used.

Before proceeding with the implant of the device 1, the zone of the articulation with the damaged cartilage is cleaned. In other words, fragments of cartilage and damaged strips thereof still fixed to the bone are removed.

Also before implantation, preferably, one or more holes can be made in the bone "O" in the zone intended to be covered by the piece 2. The maximum depth of such holes "F" is 3 cm.

The depth of the holes "F" is such to allow the flow of cells and proteins from within the bone "O" itself towards the piece 2 in order to facilitate the reconstruction of the new cartilage.

This completed, the piece is fixed on the bone "O" at the zone to be reconstructed.

For such purpose, the fibrin glue is arranged on the bone "O" in a finite number of points and then the piece 2 is applied.

Subsequently and preferably, further constraining means 3 are applied, such as the abovementioned screws and/or anchors and/or staples and/or pins.

The application of these further constraining means 3 depends on the extension of the piece 2 and on the position and on the form of the zone of the bone "O" to be covered.

Such operation of application of the device 1 can occur during arthroscopy or arthrotomy depending on the articulation involved or other factors evaluated in each instance by the doctor.

At the same time as the reconstruction of the cartilage tissue, the dissolution process of the piece 2 proceeds over the course of approximately one month. In other words, the piece 2—as it dissolves—gives way to the constructed cartilage.

The invention thus described attains the pre-established objects.

Indeed, the described use of the resorbable device for the reconstruction of cartilage allows avoiding the culture which, being quite extensive, is an extremely long, costly and complex operation.

It is also possible to prevent the periodic patient visits for the subsequent intra-articular injections.

The reconstruction of the cartilage is indeed ensured by the blood with which the piece is impregnated and by the proteins coming directly from the perforated bone.

The invention claimed is:

1. A resorbable device for the reconstruction of cartilage consisting of:
   a resorbable piece of fabric textured and made of PGA fixable to a bone at an articulation, said piece of fabric being impregnated with blood and collagen, wherein the resorbable device is configured for the PGA to dissolve giving way to the constructed cartilage in approximately one month, and
   wherein the fabric of said piece is woven fabric made of monofilament,
   wherein the fabric of said piece is of warp knitted type,
   wherein the thickness of the fabric of said piece is between 0.1 mm and 2 mm, and
   optionally constraining means for fixing said piece to said bone.

2. The device according to claim 1, wherein the fabric of said piece is obtained with a thread having a density between 50 and 200 denier.

3. The device according to claim 1, wherein the constraining means for fixing said piece to said bone is present.

4. The device according to claim 3, wherein said constraining means is fibrin glue.

5. The device according to claim 3, wherein said constraining means is at least one member selected from the group consisting of screws, anchors, staples, and pins.

6. A resorbable device for the reconstruction of cartilage consisting of:
   a resorbable piece of fabric textured and made of PGA fixable to a bone at an articulation, said piece of fabric being impregnated with blood and collagen,
   wherein the resorbable device is configured for the PGA to dissolve giving way to the constructed cartilage in approximately one month, and
   wherein the fabric of said piece is woven fabric made of monofilament,
   wherein the fabric of said piece is of warp knitted type,
   wherein the thickness of the fabric of said piece is between 0.1 mm and 2 mm, and
   optionally constraining means for fixing said piece to said bone,
   wherein said piece is impregnated with patient blood before being fixed to the bone.

7. The device according to claim 1, wherein the thickness of the fabric of said piece is between 0.3 mm and 0.6 mm.

8. The device according to claim 1, wherein the thickness of the fabric of said piece is between 0.4 mm and 0.53 mm.

9. The device according to claim 1,
   wherein said piece of fabric is impregnated with patient blood and porcine collagen, and
   wherein said constraining means is present and consists of fibrin glue for fixing said piece of fabric to said bone.

10. The device according to claim 3, wherein said constraining means is at least one resorbable member selected from the group consisting of resorbable screws, anchors, staples, and pins.

11. The device according to claim 1, wherein said piece of the fabric being impregnated with collagen is a sheet of said fabric, wherein the fabric is warp knitted fabric having a weft providing interstitial space less than 200 μm, wherein the fabric is obtained with a thread having a density between 50 and 200 denier, and wherein the fabric is between 0.3 and 0.6 mm thick.

12. The device according to claim 11, wherein the constraining means for fixing said piece to said bone is present and selected from fibrin glue and at least one resorbable member made of PGA selected from the group consisting of screws, anchors, staples and pins.

13. The device according to claim 1, wherein the constraining means for fixing said piece to said bone is present and selected from at least one member selected from the group consisting of fibrin glue, screws, anchors, staples, and pins.

14. The device according to claim 1, wherein the constraining means for fixing said piece to said bone is present and selected from fibrin glue and at least one member selected from the group consisting of screws, anchors, staples and pins.

15. The device according to claim 6, wherein said piece of the fabric being impregnated with collagen is a sheet of said fabric, wherein the fabric is warp knitted fabric having a weft providing interstitial space less than 200 μm, wherein the fabric is obtained with a thread having a density between 50 and 200 denier and wherein the fabric is between 0.3 and 0.6 mm thick.

16. The device according to claim 6, wherein the constraining means for fixing said piece to said bone is present and selected from at least one member selected from the group consisting of fibrin glue, screws, anchors, staples, and pins.

17. The device according to claim 1, wherein the entire said single piece of fabric is woven, wherein the single piece of woven fabric has first and second opposed exposed surfaces, wherein the first exposed surface is for contacting a first bone of the articulation and the second exposed surface facing away from the first bone for contacting a second said device.

18. The device according to claim 16, wherein the constraining means for fixing said piece to said bone is present and is fibrin glue.

* * * * *